United States Patent
Fourre et al.

(10) Patent No.: US 11,928,883 B2
(45) Date of Patent: Mar. 12, 2024

(54) ERGONOMIC BIOMETRIC PRINT CAPTURE DEVICE

(71) Applicant: IDEMIA IDENTITY & SECURITY FRANCE, Courbevoie (FR)

(72) Inventors: Joël-Yann Fourre, Courbevoie (FR); Elise Le Gouil, Courbevoie (FR); Mokrane Malek, Courbevoie (FR)

(73) Assignee: IDEMIA IDENTITY & SECURITY FRANCE, Courbevoie (FR)

( * ) Notice: Subject to any disclaimer, the term of this patent is extended or adjusted under 35 U.S.C. 154(b) by 0 days.

(21) Appl. No.: 17/880,022

(22) Filed: Aug. 3, 2022

(65) Prior Publication Data
US 2023/0039567 A1 Feb. 9, 2023

(51) Int. Cl.
*G06V 40/13* (2022.01)
*G06F 3/042* (2006.01)
*G06V 40/60* (2022.01)

(52) U.S. Cl.
CPC ........ *G06V 40/1312* (2022.01); *G06F 3/0421* (2013.01); *G06V 40/1318* (2022.01); *G06V 40/63* (2022.01)

(58) Field of Classification Search
CPC .............................. G06V 40/13; G06V 40/63
See application file for complete search history.

(56) References Cited

U.S. PATENT DOCUMENTS

| | | | |
|---|---|---|---|
| 2005/0254695 A1 | 11/2005 | Nagasaka et al. | |
| 2006/0165261 A1 | 7/2006 | Pira | |
| 2014/0044323 A1* | 2/2014 | Abramovich | G06V 40/1312 382/124 |
| 2020/0202101 A1* | 6/2020 | Howell | G06V 40/1312 |

FOREIGN PATENT DOCUMENTS

| | | |
|---|---|---|
| DE | 10 2014 008 160 A1 | 12/2015 |
| FR | 3 070 522 A1 | 3/2019 |
| KR | 10-0937800 B1 | 10/2009 |

OTHER PUBLICATIONS

Preliminary Search Report and Written Opinion dated Apr. 11, 2022, in French Patent Application No. 21-08507 filed Aug. 5, 2021, citing documents 1, 2, 15, 16, and 17 therein, 15 pages.

* cited by examiner

*Primary Examiner* — Joseph R Haley
(74) *Attorney, Agent, or Firm* — Oblon, McClelland, Maier & Neustadt, L.L.P.

(57) ABSTRACT

A device for capturing a biometric print of a user, the user compartment including a frontal opening designed for the passage of part of a hand into said user compartment and a lateral opening allowing the passage of the thumb of the user's hand, the lateral opening extending as far as the frontal opening to form a continuous open space, the lateral opening being delimited in a direction of insertion of the user's hand into the user compartment by a user hand positioning stop.

11 Claims, 9 Drawing Sheets

ERGONOMIC BIOMETRIC PRINT CAPTURE DEVICE

The invention relates to the field of devices for capturing a biometric print of part of a hand such as the palm of the hand or the digits of the hand, particularly contactlessly.

Biometric print capture devices able to acquire an image of a palmprint of a hand, using contact, are known from the prior art. In order to acquire a good-quality image of a palmprint, for the purposes of biometric authentication, it is desirable for the thumb of the hand to be spread away from the index finger of said hand in order to keep the skin between said thumb and said index finger taut to prevent the creation of skin folds. Thus, known devices display a hand template in which the thumb is spread away from the index finger, the user being invited to place their hand on the template for the acquisition of the image of the biometric print. The hand is thus well positioned for the acquisition of an image of a biometric print. One problem with such a solution is that the user places their hand on a surface of the device, and so the acquisition is not performed without contact with the device. For hygiene purposes, it is preferable to favour the use of contactless solutions in order to avoid surfaces touched by successive users becoming contaminated with pathogenic agents. Another problem with such a solution is that the shape of the flat surface of the device is ill suited to the palm of a hand, which is curved. Contact between the palm and the device over the entire surface is guaranteed only if the users hand is compressed against the surface of said device.

Biometric print capture devices able to acquire an image of a handprint or a print of part of a hand, contactlessly, are known from the prior art. These devices do not encourage the user to spread the thumb away from the index finger intuitively, neither do they encourage good natural positioning of the hand part with respect to said device. They require the user to be guided by a qualified operator in order to ensure that a good-quality image of a palmprint of the hand is acquired.

The invention seeks to solve the aforementioned problems of the prior art by proposing a solution that is ergonomic and intuitive for the user for acquiring a quality image of a biometric print.

The invention relates to a device for the capture of a biometric print of part of a user's hand, comprising an electronic compartment and a user compartment, the user compartment comprising a frontal opening designed for the passage of the part of a hand into said user compartment, the electronic compartment comprising acquisition means for acquiring an image of a print of said hand part, the user compartment comprising at least one lateral opening allowing the passage of the thumb of the user's hand, the lateral opening extending as far as the frontal opening to form a continuous open space, the lateral opening being delimited in a direction of insertion of the user's hand into the user compartment by a user hand positioning stop.

According to one aspect of the invention, the biometric print capture device is a contactless device.

According to one aspect of the invention, the user compartment comprises an acquisition zone delimited on the side of the frontal opening by a limit, the positioning stop being located at a stop distance of between fifty and eighty millimetres from said limit.

According to one aspect of the invention, the user compartment comprises a through-orifice able to allow one end of said user's hand to protrude beyond said user compartment, the through-orifice facing the frontal opening.

According to one aspect of the invention, the user compartment comprises an upper face comprising a transparent portion allowing the user to see at least a portion of the hand part in order to adjust its position within said user compartment.

According to one aspect of the invention, the electronic compartment comprises lighting means able to generate at least one beam of light shining towards the user compartment.

According to one aspect of the invention, the user compartment comprises means for at least partially blocking a beam of light coming from the electronic compartment at the transparent portion.

According to one aspect of the invention, the user compartment comprises a blocking hood able to block a beam of light coming from the electronic compartment at least at one of the openings that are the lateral opening and the frontal opening.

According to one aspect of the invention, the user compartment comprises a blocking hood able to block a beam of light coming from the electronic compartment at least at one of the openings that are the lateral opening, the frontal opening and the through-orifice.

According to one aspect of the invention, the user compartment comprises a lateral face comprising said lateral opening extending from the frontal opening of the user compartment as far as the positioning stop.

According to one aspect of the invention, the lateral opening is delimited by the positioning stop, a top edge and a bottom edge.

According to one aspect of the invention, at least one of the edges that are the top edge and the bottom edge is arranged in such a way as to define a natural mean hand-positioning plane substantially parallel to at least one of the edges.

According to one aspect of the invention, at least one of the edges that are the top edge and the bottom edge is arranged in such a way as to define a natural mean hand-positioning plane substantially equidistant from the top edge and from the bottom edge.

According to one aspect of the invention, the biometric print capture device comprises two lateral openings, one on each side of the frontal opening, a first lateral opening allowing the passage of the thumb of the user's right hand, a second lateral opening allowing the passage of the thumb of the user's left hand.

According to one aspect of the invention, the biometric print capture device comprises means for informing a user of an end of an acquisition session by the acquisition means, according to a distance between said hand part and the positioning stop.

Further advantages and features of the invention will become apparent from reading the description and studying the drawings.

FIG. 5b depicts a natural positioning plane for positioning a hand inside the device of FIG. 5a.

FIGS. 1, 3 and 4 depict a biometric print capture device 1 according to the invention.

The biometric print capture device 1 is able to acquire an image of a print of part of a user's hand, for example a hand, the palm of a hand, or one or more of the digits of a hand.

In particular, the device is designed to acquire a hand part that is part of the palm of a hand or the entire palm of a hand.

An image of a print is, for example, an image of a network of ridges and/or furrows in the skin, or a network of veins present in the hand.

The biometric print capture device 1 is divided into a user compartment 10 and an electronic compartment 20.

The division of the biometric print capture device 1 into a user compartment 10 and an electronic compartment 20 is a functional division.

For example, the biometric print capture device 1 may comprise a single substantially parallelepipedal unit comprising walls common to the user compartment 10 and to the electronic compartment 20 or else may be an assembly of a physical user-compartment unit and of a different physical electronic-compartment unit.

Figure 3:
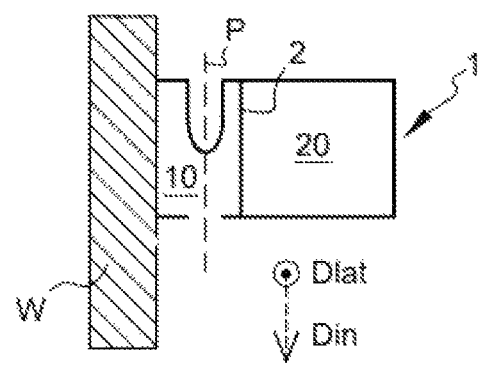
FIG. 3 depicts a biometric print capture device according to the invention, fixed against a wall.

The user compartment 10 and the electronic compartment 20 may be partitioned off from one another, for example by a dividing window 2 as depicted in FIG. 3. The dividing window may be positioned at the junction between two different physical compartments, or located in one of the compartments that are the user compartment 10 and the electronic compartment 20.

Figure 1:
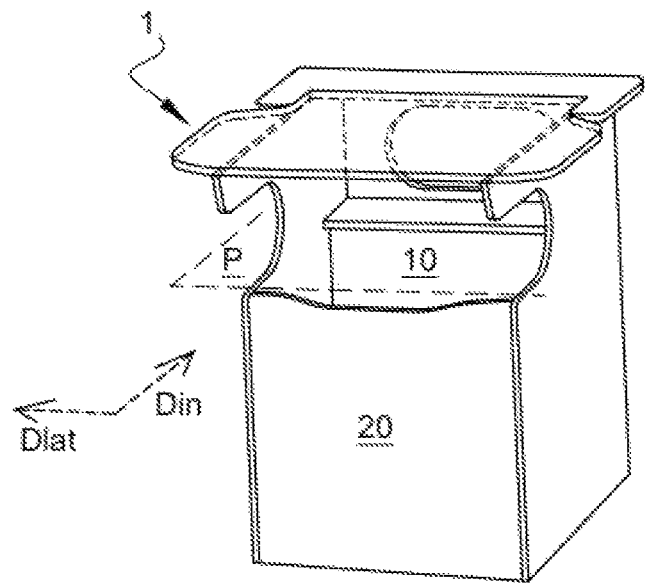
FIG. 1 depicts a biometric print capture device according to the invention, placed on a flat horizontal surface.

The user compartment 10 and the electronic compartment 20 may be open onto one another as depicted in FIG. 1, without a physical partition between them.

The user compartment 10 is able to accept within it part of a user's hand on a natural mean hand-positioning plane P, for the purposes of the electronic compartment 20 contactlessly capturing a biometric print.

The biometric print capture device 1 is contactless in so far as the capture of the biometric print is performed without contact between the part of the hand and an acquisition surface, unlike a capture device using contact which comprises an acquisition surface intended to have part of a hand press against it for the purpose of acquisition thereof.

The part of a user's hand the biometric print of which is to be imaged, for example the palm of a hand, needs to face towards the electronic compartment 20.

The natural mean hand-positioning plane P is defined by the two directions below:
   a direction of insertion Din of the hand into the user compartment 10,
   a lateral direction Dlat perpendicular to the direction of insertion Din.

FIG. 1 illustrates a biometric print capture device 1 placed on a flat surface such as a table or the ground. The natural mean hand-positioning plane P is horizontal.

Figure 2:
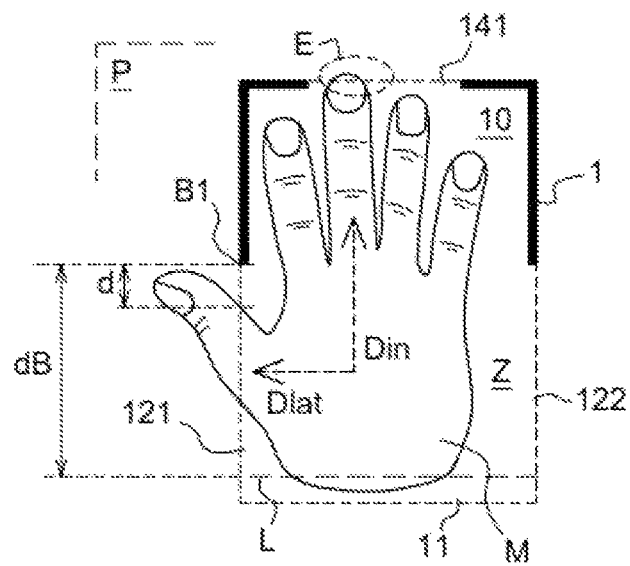
FIG. 2 depicts a user's hand inside the user compartment of the biometric print capture device.

FIG. 2 illustrates a view from above and in section on the positioning plane P, of a hand M placed inside the user compartment 10 of the biometric print capture device 1 according to FIG. 1, for the purpose of biometrically capturing the palm of the hand. The hand M is positioned on a positioning plane P. The palm of the hand faces towards the electronic compartment 20. The direction of insertion Din extends in a longitudinal direction of the hand, namely a direction extending from the user's wrist to the middle finger of the hand. The lateral direction Dlat extends in a lateral direction of the hand, namely a direction extending from the little finger to the thumb, in a direction perpendicular to the direction of insertion Din:

According to FIG. 3, the biometric print capture device 1 is fixed to a wall W. The natural mean hand-positioning plane P is vertical.

Figure 4:
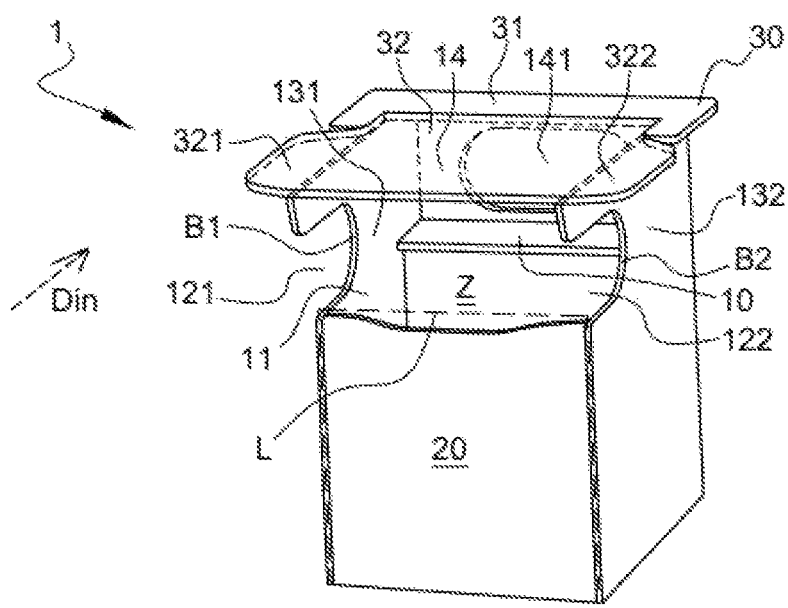
FIG. 4 depicts the same device as in FIG. 1, with various constituent elements referenced.
Figure 5A:
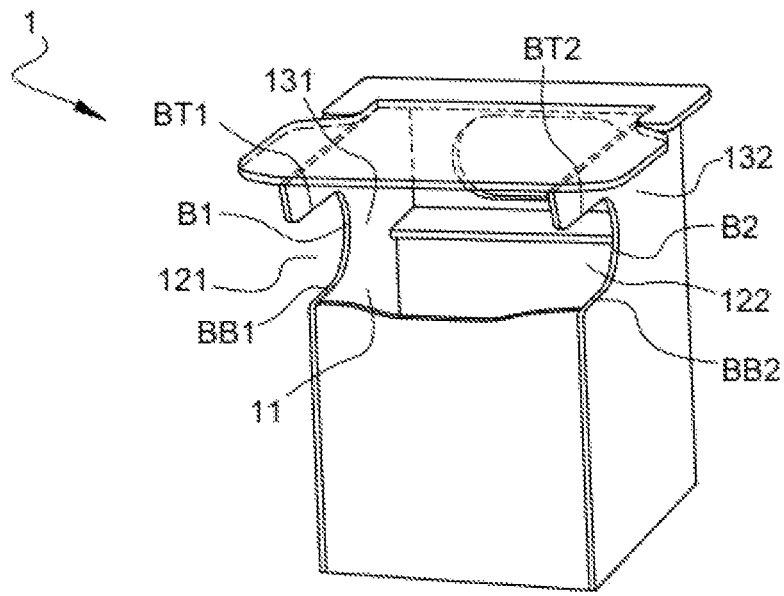
FIG. 5a depicts a first embodiment of the biometric print capture device according to the invention.
Figure 5B:
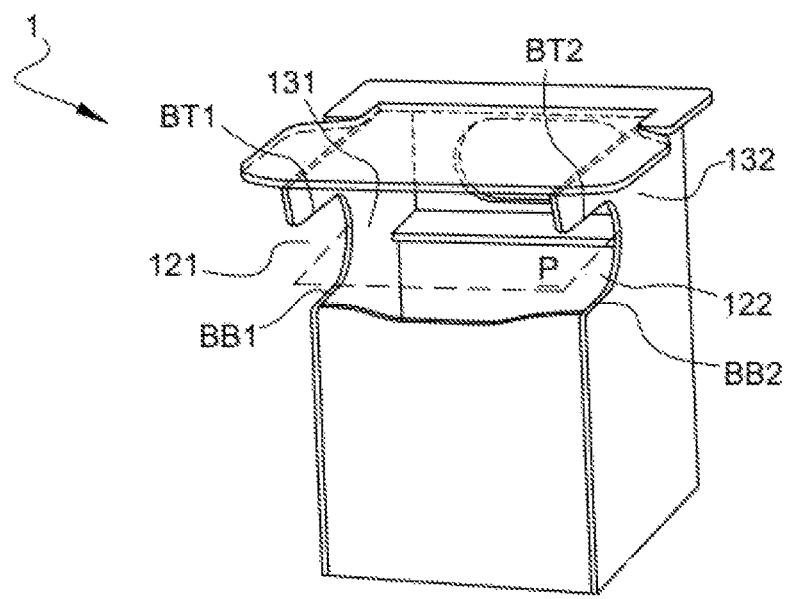

As visible in FIGS. 2 and 4, the user compartment 10 comprises a frontal opening 11 designed for the passage of the part of the user's hand.

In particular, the frontal opening 11 is designed for the passage of the palm of a user's hand.

The width of the frontal opening 11, in the lateral direction Dlat, needs to allow all sizes of hand and particularly all sizes of hand palm to be inserted into the compartment, but in order to encourage the user to insert their hand on the predetermined positioning plane P and also to spread the thumb when introducing the palm of the hand into the user compartment 10, should not be too great. For example, the width of the frontal opening 11 in the lateral direction Dlat is comprised between 100 mm and 150 mm, preferably between 120 mm and 130 mm.

Facing the frontal opening 11, the user compartment 10 optionally and advantageously comprises a through-orifice 141.

The through-orifice 141 is able to receive an end E of said user's hand M so as to allow said end E to protrude beyond the user compartment 10, as illustrated in FIG. 2.

The depth of the user compartment 10, between the frontal opening 11 and the through-orifice 141, in the direction of insertion Din may be 50 mm. In that case, the through-orifice 141 is able to allow the index, middle, ring and little finger of a hand to pass through it. The device is therefore able to acquire an image of a print of part of the palm of a hand, a plurality of acquisitions in different positions in the direction Din then being necessary in order to be able to reconstruct an image of the entire palmprint of the hand or of the entire hand including the fingers.

As a preference, the depth of the user compartment 10, between the frontal opening 11 and the through-orifice 141, in the direction of insertion Din is comprised between 120 mm and 200 mm. Depending on the size of the user's hand and on the depth of the user compartment 10, the through-orifice 141 allows one end E of the user's hand M to protrude beyond it.

Thanks to the through-orifice 141, the user is not limited in their movement in the direction of insertion Din of the hand by an obstacle which prevents said user from correctly positioning their hand in the user compartment 10 for acquiring an image of a print of the hand part that is to be imaged, in particular in this instance the palm of the hand.

The through-orifice 141 is not always necessary, for example in the case of the user compartment 10 having a depth of the order of 280 mm.

The height of the frontal opening 11 in a direction perpendicular to the direction of insertion Din and to the lateral direction Dlat needs to allow the passage of a hand, for example comprised between 50 mm and 100 mm, preferably between 60 mm and 80 mm.

According to one exemplary embodiment, the user compartment 10 comprises an end wall 14 facing the frontal opening 11, the end wall 14 comprising the through-orifice 141.

Advantageously, the through-orifice 141 is centred on the end wall 14 in a lateral direction Dlat. That makes it equally possible for an end E of a user's right hand or an end E of a user's left hand to pass through it.

Advantageously, the through-orifice 141 provides the user with a visual indication of the correct positioning of the hand, the user being able to use the through-orifice 141 as a target to aim for for said positioning of the hand.

Advantageously, the through-orifice 141 is a heightwise guide for the user's hand, namely a guide in a direction perpendicular to the palm of the hand, the user being able to use the through-orifice 141 as a guide for determining the hand-positioning plane P. As a preference, and as depicted in FIG. 4, the through-orifice 141 is of oblong shape, offering non-aggressive contours for the passage of the end E of said user's hand.

According to another exemplary embodiment, the user compartment 10 has no end wall, the user compartment being fully open on the part facing the frontal opening 11.

The user compartment 10 comprises an upper face 30.

Advantageously, the upper face 30 comprises a transparent portion 32 allowing the user to adjust the positioning of their hand or hand part inside said user compartment 10.

The upper face 30 faces the electronic compartment 20.

The upper face 30 may be parallel to the natural mean hand-positioning plane P or else may make an angle therewith, for example an angle comprised between 0 and 45 degrees. A non-zero angle between the upper face 30 and the hand-positioning plane P may make it possible to improve the ergonomics of the device, for example make it easier for the user's hand to be inserted into the user compartment 10. Another advantage to inclining the upper face 30 with respect to the positioning plane P is that of limiting potential reflections of light when the upper face 30 comprises a transparent portion 32.

As visible in FIGS. 2 and 4, the user compartment 10 comprises at least one lateral opening 121, 122 allowing the passage of the thumb of the user's hand M. The lateral opening 121, 122 extends as far as the frontal opening 11 to form a continuous open space.

Advantageously, the frontal opening 11 extends as far as the upper face 30.

Advantageously, the user compartment 10 comprises two lateral openings 121, 122, one on each side of the frontal opening 11, a first lateral opening 121 allowing the passage of the thumb of the user's right hand, a second lateral opening 122 allowing the passage of the thumb of the user's left hand.

A lateral opening 121, 122 is delimited in the direction of insertion Din of the user's hand, by a user hand positioning stop B1, B2.

A lateral opening 121, 122, in collaboration with its associated positioning stop B1, B2, encourages the user to spread the thumb of their hand away from the index finger of said hand in order to prevent creating skin folds on the palm of the hand.

The positioning stop impedes full introduction of the hand, encouraging the user to spread the thumb and also blocks the progression of the hand inside the user compartment in the direction of insertion Din when the thumb comes into abutment against the positioning stop.

The user compartment 10 comprises an acquisition zone Z delimited on the side of the frontal opening 11 by a limit L.

The positioning stop B1, B2 is advantageously located at a stop distance dB of between fifty and eighty millimetres from said limit L, preferably between sixty and seventy millimetres from said limit L, the stop distance dB being measured in a plane coplanar with the positioning plane P. Such a positioning of the positioning stop B1, B2 allows the palm of a hand, thumb spread, to be introduced into the user compartment 10 at least as far as the limit L for correct positioning for the purposes of capturing the biometric print thereof.

According to one example of a method for capturing a biometric palmprint of a hand, the user introduces their hand into the user compartment 10 in the direction of insertion Din, via the frontal opening 11. Impeded by the presence of the positioning stop B1, B2, the user is encouraged to spread the thumb away from the index finger even before coming into contact with said positioning stop B1, B2. When the image acquisition or acquisitions by the acquisition means have been completed, the device 1 signals the end of the acquisition session to the user. Thus, the user is informed that their hand has been inserted far enough into the user compartment 10 to capture a print, and that they may remove it from the user compartment 10.

The end of an acquisition corresponds for example to the palm of the users hand crossing the limit L of the acquisition zone Z.

Advantageously, the end of an acquisition session is determined when the hand part is at a distance from the positioning stop B1, B2 that is equal to a predetermined distance d of the order of one to two centimetres.

A print capture may be the result of one or a plurality of image acquisitions by the acquisition means.

Advantageously, at the end of an acquisition session, the image or images taken by acquisition means are sufficient to generate an image of the biometric print of the part of the users hand.

However, additional images may be acquired by acquisition means while the hand is being withdrawn from the user compartment 10, if necessary.

According to the advantageous positioning of the positioning stop as described hereinabove, correct positioning for capturing a print is reached before the hand part makes any contact with the positioning stop B1, B2, at a distance from the positioning stop B1, B2 that is greater than the predetermined distance d of the order of one to two centimetres, thus ensuring contactless print capture. This positioning is depicted in FIG. 2.

The signalling to the user is performed at the predetermined distance d from the positioning stop B1, B2 which is of the order of one to two centimetres.

If, despite the signalling of the end of an acquisition session, the user continues to insert the palm of their hand into the user compartment 10 in the direction of insertion Din, the positioning stop B1, B2 will halt the progression of the hand in a position in which the hand part in contact with the device remains highly localized and the contact with the device is limited to the positioning stop B1, B2.

The use of the device of the invention is more hygienic than the devices using contact that are known from the prior art, even when the user fails to withdraw their hand after said device has given the signal.

The direction of insertion Din is intuitive for the user because of the shape of the user compartment 10, the widest opening being the frontal opening, the lateral openings 121, 122 being intuitively intended for the passage of the thumb of the hand.

Nevertheless, indications or instructions indicating the direction of insertion Din to the user may be envisaged, for example via a directional indicator, a voice instruction, a depiction of a hand template within the user compartment 10, a pictogram, or even a video displayed on a screen.

FIGS. 5a to 6f illustrate a first embodiment of a lateral opening 121, 122.

The user compartment 10 comprises two lateral faces 131, 132 each comprising a lateral opening 121, 122 extending from the frontal opening 11 of the user compartment as far as the positioning stop B1, B2.

The shape of the positioning stop is defined hereinafter viewed from an angle looking from the lateral face 132 in the lateral direction Dlat, as indicated in FIGS. 6a to 6f, 7b, 8b.

Each lateral opening 121, 122 is delimited by the positioning stop B1, B2, a top edge BT1, BT2 and a bottom edge BB1, BB2.

Advantageously, for a lateral opening 121, 122, at least one of the edges BT1, BT2, BB1, BB2 that are the top edge BT1, BT2 and the bottom edge BB1, BB2 is arranged in such a way as to define a natural mean hand-positioning plane P substantially parallel to at least one of the edges or equidistant from the top edge BT1, BT2 and from the bottom edge BB1. BB2.

FIGS. 6a to 6f depict the user compartment 10 of a biometric print capture device 1 placed on horizontal ground as in FIG. 1, seen from the lateral face 132 in the lateral direction Dlat.

Figure 6A:
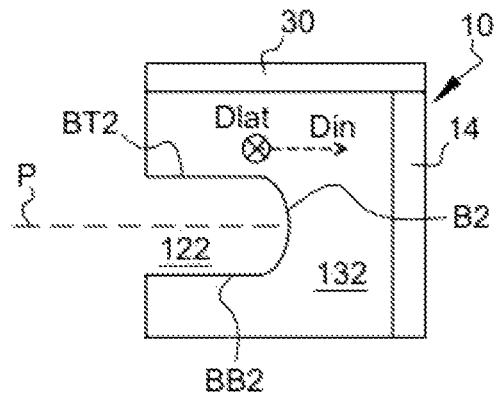
FIG. 6a illustrates a side view of a first variant of a first embodiment.

According to a first variant illustrated in FIG. 6a, the top edge BT2 and bottom edge BB2 are horizontal. The natural mean hand-positioning plane P is horizontal and parallel to the top edge BT2 and bottom edge BB2, but is also equidistant from the top edge BT2 and bottom edge BB1. The positioning stop B2 is rounded, in the shape of a U.

Figure 6B:
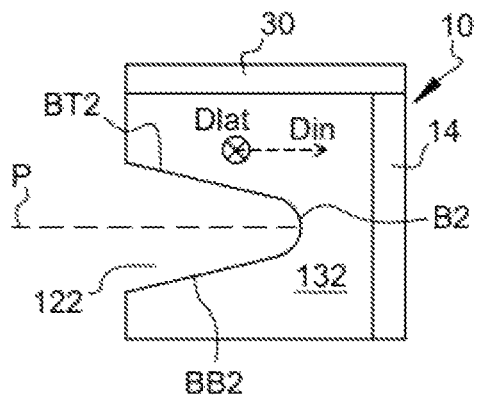
FIG. 6b illustrates a side view of a second variant of the first embodiment.

According to a second variant illustrated in FIG. 6b, the top edge BT2 is inclined at an angle that, in the trigonometrical sense, is negative with respect to a horizontal plane, the bottom edge BB2 is inclined at an angle that, in the trigonometrical sense, is positive with respect to a horizontal plane, the positive and negative angles being opposite and substantially equal in terms of absolute value, for example ten degrees or so. The natural mean positioning plane P is horizontal and located equidistant from the top edge BT2 and bottom edge BB2. The positioning stop B2 is rounded, in the shape of a U.

Figure 6C:
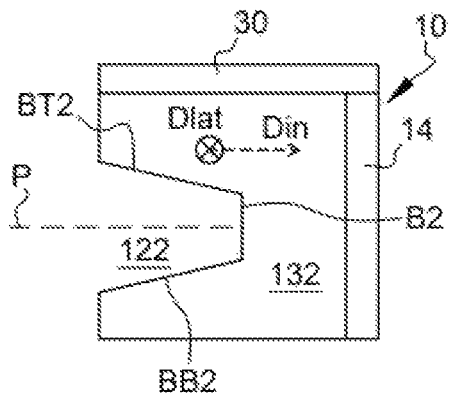
FIG. 6c illustrates a side view of a third variant of the first embodiment.

A third variant is illustrated in FIG. 6c and differs from the second variant in that the positioning stop B2 is not rounded in shape.

Figure 6D:
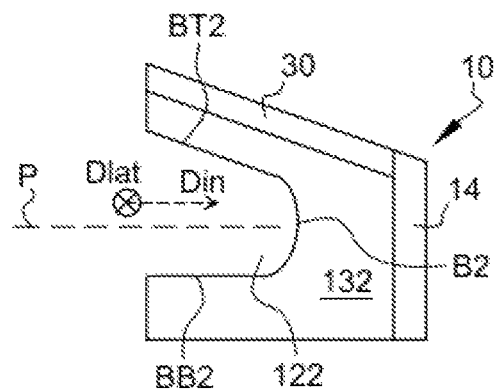
FIG. 6d illustrates a side view of a fourth variant of the first embodiment.

According to a fourth variant illustrated in FIG. 6d, the top edge BT2 is inclined at an angle that, in the trigonometrical sense, is negative with respect to a horizontal plane, for example ten degrees or so, the bottom edge BB2 being horizontal. The natural mean hand-positioning plane P is horizontal and parallel to the bottom edge BB2. The positioning stop B2 is rounded, in the shape of a U.

Figure 6E:
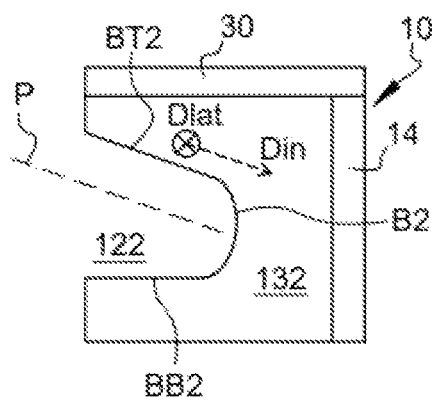
FIG. 6e illustrates a side view of a fifth variant of the first embodiment.

According to a fifth variant illustrated in FIG. 6e, the top edge BT2 is inclined at an angle that, in the trigonometrical sense, is negative with respect to a horizontal plane, and the bottom edge BB2 is horizontal. The natural mean hand-positioning plane P is inclined and parallel to the top edge BT2. The positioning stop B2 is rounded, in the shape of a U.

The overall shape of the user compartment 10, or indications using lines or drawings may encourage placement of the hand on a predetermined mean positioning plane P.

For example, a different colour along one edge of the lateral orifice 122 may encourage the placement of the hand in a mean positioning plane P that is parallel to this edge that is coloured in a particular way.

The shape of the compartment may also encourage the hand to be placed in a particular mean positioning plane P. For example, in FIGS. 6d and 6e, the natural positioning plane P differs according to the inclination of the upper face 30, the lateral opening 122 having the same shape in both instances.

Figure 6F:
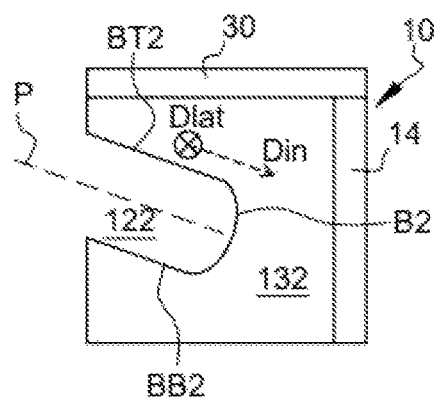
FIG. 6f illustrates a side view of a sixth variant of the first embodiment.

According to a sixth variant illustrated in FIG. 6f, the top edge BT2 and the bottom edge are inclined at the same angle that, in the trigonometrical sense, is negative with respect to a horizontal plane, for example ten degrees or so. The natural mean positioning plane P is inclined, parallel to both the top edge BT2 and the bottom edge BB2 and is located equidistant from the top edge BT2 and bottom edge BB2. The positioning stop B2 is rounded, in the shape of a U.

In general terms, it is preferable for the positioning stop B1, B2 to have a rounded shape, whatever the arrangement of the top edge BT1, BT2 and of the bottom edge B91, BB2, for reasons of ergonomics.

These six variants illustrate non-limiting examples of possible shapes for the lateral openings 121, 122. These examples are aimed at demonstrating, firstly, the influence that the shape of the lateral openings 121, 122 and of the upper face 30 has on a natural plane for the positioning of the user's hand and, secondly, that there are a multitude of possible shapes of lateral opening 121, 122.

FIGS. 7a, 7b, 8a, 8b illustrate a second embodiment of a lateral opening 121, 122.

Figure 7A:
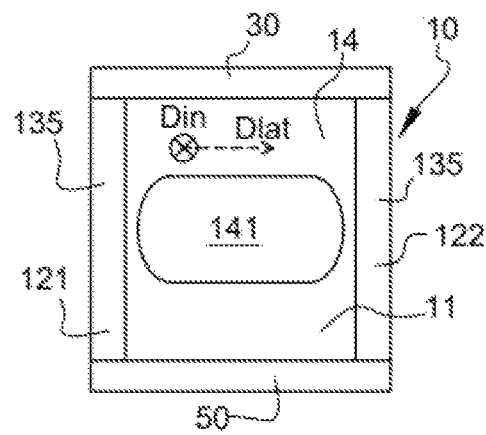
FIG. 7a illustrates a face-on view of a first variant of a second embodiment.
Figure 8A:
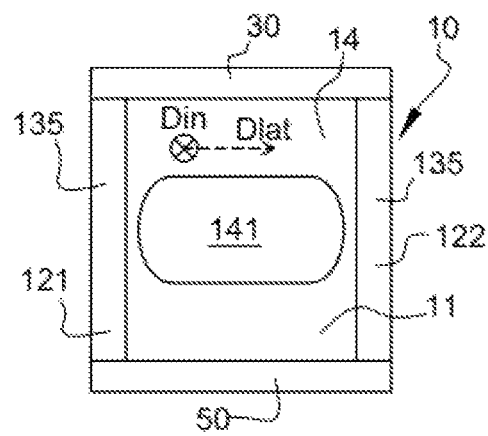
FIG. 8a illustrates a face-on view of a second variant of the second embodiment.

FIGS. 7a and 8a illustrate a user compartment 10 of a biometric print capture device 1 placed on horizontal ground as in FIG. 1, viewed from the frontal opening 11 in the direction of insertion Din. The end wall 14 comprises an oblong through-orifice 141.

Figure 7B:
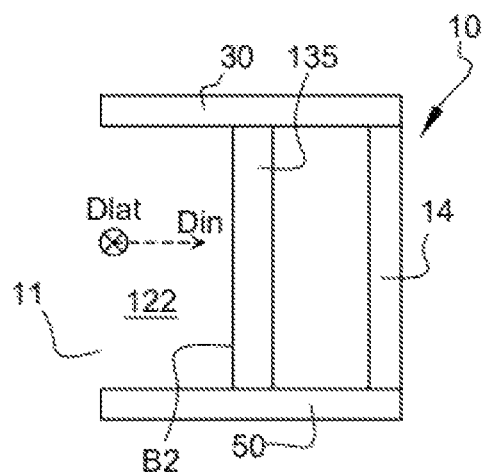
FIG. 7b illustrates a side view of the first variant of the second embodiment.
Figure 8B:
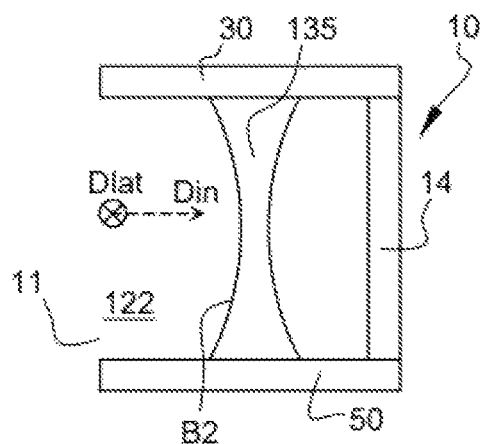
FIG. 8b illustrates a side view of the second variant of the second embodiment.

FIGS. 7b and 8b illustrate the user compartment 10 of FIGS. 7a and 8a, viewed from one side, in the lateral direction Dlat.

Unlike in the first embodiment, the user compartment 10 does not comprise two lateral faces 131, 132.

The user compartment 10 comprises two lateral openings 121, 122 delimited by two posts 135.

Each lateral opening 121, 122 is delimited by a post 135 forming the positioning stop B1, B2.

Two posts 135 extend one on each side of the frontal opening 11, from the upper face 30 of the user compartment 10 as far as the electronic compartment 20 or as far as a base 50 of the user compartment 10 which is open onto the electronic compartment 20.

According to a first embodiment variant illustrated in FIGS. 7a and 7b, each post 135 is in the form of a straight cylindrical rod.

According to a second embodiment variant illustrated in FIGS. 8a and 8b, each post 135 widens at its ends.

These two variants illustrate two non-limiting examples of possible shapes for the posts 135.

Figure 9:
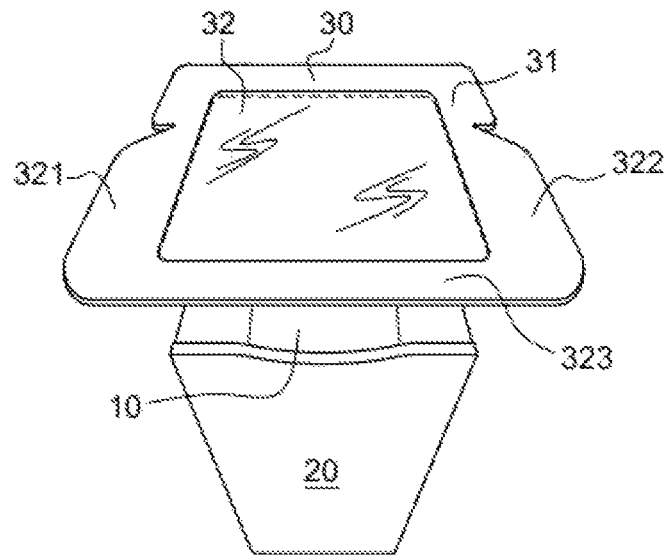
FIG. 9 depicts a biometric print capture device comprising three opaque anti-dazzle blocking hoods.
Figure 10:
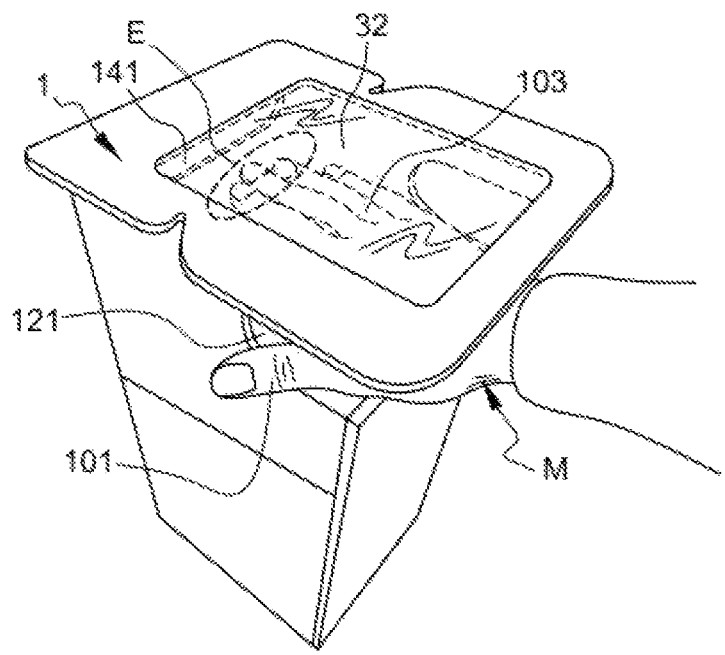
FIG. 10 depicts a user's hand inserted into the device of FIG. 9 for acquiring an image of a palmprint of a hand.

As depicted in FIGS. 9 and 10, the upper face 30 comprises a transparent portion 32 allowing the user to at least partially see their hand in order to adjust its position within said user compartment 10.

The transparent portion 32 is able to transmit at least 10% of the light that it receives.

Advantageously, the transparent portion 32 allows the user introducing part of their hand into the user compartment 10 to see the through-orifice 141 of said user compartment 10.

Advantageously, the transparent portion 32 allows the user introducing part of their hand into the user compartment 10 to see the positioning stop B1, B2 of the lateral opening 121, 122.

The electronic compartment 20 comprises lighting means able to generate at least one beam of light shining towards the user compartment 10 in order to illuminate part of a hand inserted into the user compartment 10 for the purposes of acquiring an image of a print thereof. The electronic compartment 20 comprises acquisition means comprising a camera.

The camera has an optical axis preferably directed perpendicular to the hand-positioning plane P.

According to one exemplary embodiment, the lighting means are able to generate several collinear beams of light positioned in a ring around the camera.

According to another exemplary embodiment, the lighting means are able to generate a single beam of light that is inclined by an angle of between 10° to 30° with respect to an optical axis of the camera.

The lighting means may be able to generate soft light, for example diffused through a diffuser positioned in front of a light source. Alternatively, the lighting means may comprise a transparent blade into which light is injected, the transparent blade having on one face diffusing parts arranged in such a way as to generate a diffused beam of light exiting said blade. The lighting means may also comprise large-sized light sources, for example lighting panels using OLED technology.

In the event that it is a biometric print of a network of veins in the digits or the palm of the hand that is being captured, the lighting means are advantageously able to generate at least one beam of light that is infrared and polarized in a predetermined direction, the acquisition means comprising a polarizer orthogonal to said predetermined direction.

In the case that it is a biometric print of a network of ridges and/or furrows in the skin that is being captured, the lighting means are advantageously able to generate at least one beam of light in the visible spectrum, advantageously in green or blue, and which is polarized in a predetermined direction, the acquisition means comprising a polarizer parallel to said predetermined direction.

As a preference, a dividing window 2 present between the user compartment 10 and the electronic compartment 20 is inclined with respect to the natural mean hand-positioning plane P so as to avoid or limit direct reflections of said beam of light towards the camera.

Likewise, having the upper face 30 inclined with respect to the positioning plane P avoids or limits, when this face comprises a transparent portion 32, reflections of said beam of light towards the camera.

Advantageously, the user compartment 10 comprises means for at least partially blocking the beam of light generated by the lighting means, at the transparent portion 32.

For example, the blocking means comprise a strip of microshutters able to filter the light coming from the at least one beam of light, in a direction that is dependent on the orientation of said microshutters. In that case, during use of the biometric print capture device 1, the direction of said beam of light and a direction in which the user gazes towards the device are advantageously different.

According to another example, the blocking means comprise means for spectral selection of the at least one beam of light. For example, the lighting means are able to generate at least one beam of light of a first colour, such as blue, and the upper face 30 comprises a transparent portion 32 that is tinted in another colour, such as yellow.

According to another example, the blocking means comprise polarizing means. For example, the lighting means are able to generate at least one linearly polarized beam of light, and an orthogonal polarizer is located against the transparent portion 32 of the upper face 30. Advantageously, the lighting means are able to generate another, unpolarized, beam of light visible to the user.

In general, the transparent portion 32 of the upper face 30 may comprise a tinted window.

The upper face 30 may comprise a semi-opaque or opaque portion 31 able to block out at least 95% of the light passing through it, or not letting any light through at all.

Advantageously, as depicted in FIG. 6d, the upper face 30 of the user compartment 10 is inclined so that the user compartment is bulkier near the frontal opening 11 than near the end wall 14.

Such an arrangement is ergonomic because it allows the user compartment 10 intended to receive part of a hand to have a wider opening near the wrist, which is thicker than the end of the fingers of said hand.

In addition, when the upper face 30 comprises a transparent portion 32, the inclination of said upper face may make it possible to eliminate or limit direct reflections of a beam of light from the lighting means towards a camera of the acquisition means.

In the figures, the transparent portion 32 is coplanar with the semi-opaque or opaque portion 31.

However, for further limiting direct reflections of a beam of light from the lighting means towards a camera of the acquisition means, it may be advantageous for the transparent portion 32 not to be coplanar with the semi-opaque or opaque portion 31.

For example, the transparent portion 32 is inclined with respect to the positioning plane P at a first angle so as to limit the reflections of light towards the acquisition means, whereas the rest of the upper face which comprises the semi-opaque or opaque portion 31 is inclined with respect to the positioning plane P at a second angle different from the first angle, so as to give the user compartment 10 a shape that is ergonomic for passing a hand into it, through the frontal opening 11.

The semi-opaque or opaque portion 31 may also be parallel to the positioning plane P, the second angle then being equal to zero.

Advantageously, the user compartment 10 comprises a blocking hood 321, 322, 323 at least at one of the openings that are the lateral opening 121, 122 and the frontal opening 11.

A blocking hood 321, 322, 323 is able to block out at least part of a beam of light generated by the lighting means of the electronic compartment 20, at an opening. In other words, a blocking hood 321, 322, 323 is able to block out at least part of a beam of light exiting via an opening.

Thus, light coming from the electronic compartment 20 and passing through said openings does not dazzle the user. The technical effect of the blocking hood 321, 322, 323 is that it has an anti-dazzle effect towards the user.

The user compartment 10 may also comprise a blocking hood at the through-orifice 141 (such a hood is not depicted in the figures).

In instances in which the user compartment 10 does not comprise an end wall, a blocking hood may be located at the opening facing the frontal opening 11. As a preference, the upper face 30 comprises said blocking hood 321, 322, 323.

Figure 11:
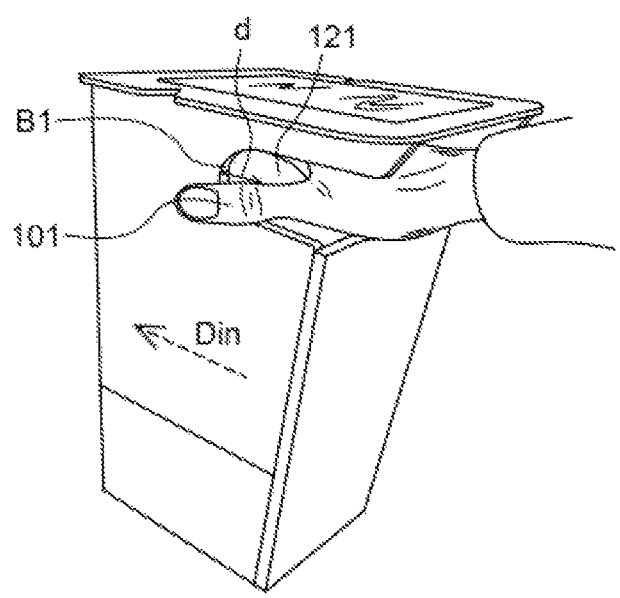
FIG. 11 depicts another view of FIG. 10.

In FIGS. 9, 10 and 11, the upper face 30 extends beyond the lateral faces 131, 132 of the user compartment and in front of the frontal opening 11, the protruding parts forming blocking hoods 321, 322, 323.

In FIGS. 9, 10 and 11, a blocking hood 321, 322, 323 is formed as an integral part of the semi-opaque or opaque portion 31 of the upper face 30.

In FIGS. 1, 4, 5a and 5b, a blocking hood 321, 322, 323 is formed as an integral part of the transparent portion 32 of the upper face 30.

Whether or not it is an integral part of the transparent portion 32, in instances in which the blocking hood 321, 322, 323 is transparent and after the manner of the blocking means of the transparent portion 32, the blocking hood is able to block out the light through spectral selection, through polarization, or through angular selection with microshutters or interference filters.

Alternatively, a blocking hood 321, 322, 323 may be distinct from the upper face 30 and mounted fixedly or movably on the user compartment 10, for example on the upper face 30 or a lateral face 131, 132.

Advantageously, as depicted in FIGS. 9 to 11, the user compartment 10 comprises three blocking hoods: a first blocking hood 321 located at a first lateral opening 121, a second blocking hood 322 located at a second lateral opening 122 and a third blocking hood 323 located at the frontal opening 11.

It is not always beneficial for the user compartment 10 to comprise a blocking hood 321, 322, 323. In particular, in instances in which the beam of light generated by the compartment 20 is a beam of infrared or ultraviolet light, the problem of dazzling the user does not arise. This applies for example, in the case of a device for capturing a biometric print of a network of veins in the digits or the palm of a hand.

Advantageously, the wavelength for an infrared beam is comprised between 700 and 2000 nm, preferably between 700 and 1050 nm.

Advantageously, the wavelength for an ultraviolet beam is comprised between 320 and 400 nm, preferably between 370 and 400 nm.

Advantageously, the light external to the biometric print capture device 1 and transmitted by the transparent portion is blocked by the acquisition means. The acquisition means may thus comprise a spectral filter, microshutters, an interference filter configured to perform angular selection or incorporate a polarizer.

The electronic compartment 20 comprises:
acquisition means for acquiring an image of a print of part of a user's hand,
means for illuminating said hand part.

The acquisition means comprise a camera able to acquire an image in the acquisition zone Z of the user compartment 10.

The acquisition means may comprise a plurality of cameras for acquiring a plurality of images of a plurality of subzones of the acquisition zone Z, the plurality of subzones covering the acquisition zone Z, the optical axes of the cameras being collinear or otherwise.

The acquisition means may comprise a plurality of cameras for acquiring a plurality of images from a plurality of viewpoints, one camera being for example able to acquire an image of a writer's palm and/or with a view to reconstructing a three-dimensional image. The writer's palm is the area on the side of the palm which normally rests against the paper when writing.

The lighting means are able to generate at least one beam of light shining towards the user compartment to illuminate said part of the hand introduced into the user compartment 10 with a view to acquiring an image of its print.

The combination of the acquisition means and of the lighting means makes it possible to obtain good-quality images of the print for the purposes of subsequent user authentication.

Advantageously, the biometric print capture device 1 comprises means for informing the user that they can withdraw their hand, their palm, their finger or fingers from the user compartment 10 once one or a plurality of images has or have been acquired by the acquisition means and thus halt the progression of their hand, their palm or their fingers inside the user compartment in the direction of insertion Din of the hand.

According to one example of the acquisition of an image of a biometric print of the four fingers, the index, middle, ring and little finger and of the palm of a hand, image acquisitions by the acquisition means begin as soon as the longest finger of the hand crosses the limit L of the acquisition zone Z. The hand progresses inside the user compartment of the device in the direction of insertion Din. When the image acquisitions are complete, the device informs the user that they may remove their hand.

If the acquisition zone Z does not cover the entirety of the part of the hand of which the print is to be captured by the device, the acquisition means may acquire a plurality of images as the hand progresses inside the user compartment 10. Thereafter, the images are assembled to reconstruct the image of the complete biometric print of said hand part.

Correct placement for the acquisition of a biometric print of the palm of the hand corresponds for example to a distance between said hand and the positioning stop B1, B2 that is less than or equal to a predetermined distance d as indicated in FIG. 2 and FIG. 11.

The distance between the hand and the positioning stop B1, B2 may be determined by an optical sensor such as a telemeter or a camera, or by detecting the breaking of an infrared beam located in the vicinity of the positioning stop B1, B2.

A camera of the acquisition means 20 may for example be used to determine said distance between the hand and the positioning stop B1, B2.

The means for informing the user that they may withdraw their hand comprise for example means for sending an audible signal, for displaying a message or a pictogram, or else for illuminating an illuminated indicator.

The lateral positioning of the hand, in the lateral direction Dlat, inside the user compartment 10 does not need to be checked because the positioning stop B1, B2 and/or the lateral face 131, 132 forces the part of the hand that is inside the user compartment 10 to remain in the acquisition zone Z, particularly in cases in which the thumb of the hand is positioned in a lateral opening 121, 122 during an acquisition of the palm of a hand or of the four fingers, index, middle, ring and little finger of the hand.

FIGS. 10 and 11 illustrate a user's hand M inside a biometric print capture device according to the invention. The user's thumb 101 is spread away from the other fingers 103 of the hand.

As visible in FIG. 10, the user can partly see their hand, through the transparent portion 32 of the upper face 30 of the user compartment 10. The end E of said user's hand is visible to the user, as is part of the through-orifice 141. The thumb 101 is located in the lateral opening 121 of the user compartment.

As visible in FIG. 11, the user's hand has been introduced in a direction of insertion Din and is located inside the user compartment. The thumb 101 is located at a non-zero distance d from the positioning stop B1 of the lateral opening 121 of the user compartment.

Note that the user is encouraged to spread their thumb 101 away from the other fingers 103 of their hand M because otherwise this user would be impeded by the positioning stop B1 in their attempt to completely introduce their hand into the user compartment.

Note also that the user cannot introduce their hand very far into the user compartment in the direction of insertion Din because they are impeded by the positioning stop B1, which will block the progression of their hand inside said user compartment.

Thus, the positioning stop B1 encourages the user to spread their thumb 101 away from the other fingers of their hand M and allows correct positioning inside the user compartment 10, it being possible for said positioning to be checked thanks to the transparent portion 32 of the upper face 30 of the user compartment 10, which allows the user to at least partially see their hand inside said user compartment 10.

Optionally, the device of the invention may comprise a screen located for example above the user compartment, to guide the user in the successive hand placements to be performed inside the user compartment.

The device of the invention is particularly well suited to capturing a biometric print of the palm of a hand.

The device of the invention may also be used for capturing a biometric print of the two thumbs of a user's two hands, the lateral openings 121, 122 allowing the thumbs to enter the user compartment 10, the other fingers being positioned outside the user compartment 10, with the palms of the two hands facing one another.

The lateral opening 11 allows the passage of one or more fingers for capturing fingerprints, as known in the prior art.

The invention claimed is:

1. A device for contactless capture of a biometric print of part of a user's hand, able to acquire a part of a hand being part of a palm of a hand, comprising:
an electronic compartment and a user compartment,
the user compartment including a frontal opening designed for passage of the palm of a hand into said user compartment,
the electronic compartment including acquisition means for acquiring an image of a print of said hand part, and
the user compartment further including at least one lateral opening allowing the passage of a thumb of the user's hand,
wherein the lateral opening extends as far as the frontal opening to form a continuous open space, the lateral opening being delimited in a direction of insertion of the user's hand into the user compartment by a user hand positioning stop to encourage the palm of the hand to be introduced into the user compartment with the thumb spread, the positioning stop impeding full insertion of the hand,
wherein the user compartment further includes an acquisition zone delimited on a side of the frontal opening by a limit, the positioning stop being located at a stop distance of between fifty and eighty millimetres from said limit.

2. The biometric print capture device according to claim 1, wherein the user compartment further includes a through-orifice able to allow one end of said user's hand to protrude beyond said user compartment, the through-orifice facing the frontal opening.

3. The biometric print capture device according to claim 1, wherein the user compartment further includes an upper face having a transparent portion allowing the user to see at least a portion of the hand part in order to adjust its position within said user compartment.

4. The biometric print capture device according to claim 1, wherein the electronic compartment further includes lighting means for generating at least one beam of light shining towards the user compartment, the user compartment including means for at least partially blocking a beam of light coming from the electronic compartment at a transparent portion.

5. The biometric print capture device according to claim 1, wherein the user compartment further includes a blocking hood able to block a beam of light coming from the electronic compartment at least at one of the openings that are the lateral opening and the frontal opening.

6. The biometric print capture device according to claim 1, wherein the user compartment further includes a lateral face having said lateral opening extending from the frontal opening of the user compartment as far as the positioning stop.

7. The biometric print capture device according to claim 1, wherein the lateral opening is delimited by the positioning stop, a top edge and a bottom edge, at least one of edges that are the top edge and the bottom edge being arranged in such a way to define a natural mean hand-positioning plane substantially parallel to at least one of the edges or equidistant from the top edge and from the bottom edge.

8. The biometric print capture device according to claim 1, further comprising two lateral openings, one on each side of the frontal opening, a first lateral opening allowing the passage of the thumb of the user's right hand, and a second lateral opening allowing the passage of the thumb of the user's left hand.

9. The biometric print capture device according to claim 1, further comprising means for informing a user of an end of an acquisition session by the acquisition means, according to a distance between said hand part and the positioning stop.

10. A device for contactless capture of a biometric print of part of a user's hand, comprising:
an electronic compartment and a user compartment,
the user compartment including a frontal opening designed for passage of a hand into said user compartment, the electronic compartment including acquisition means for acquiring an image of a print of said hand part, and the user compartment further including at least one lateral opening allowing the passage of a thumb of the user's hand, wherein the lateral opening extends as far as the frontal opening to form a continuous open space, the lateral opening being delimited in a direction of insertion of the user's hand into the user compartment by a user hand positioning stop to encourage the hand to be introduced into the user compartment with the thumb spread, the positioning stop impeding full insertion of the hand, wherein the user compartment further includes a through-orifice able to allow one end of said user's hand to protrude beyond said user compartment, the through-orifice facing the frontal opening.

11. A device for contactless capture of a biometric print of part of a user's hand, comprising:

an electronic compartment and a user compartment, the user compartment including a frontal opening designed for passage of a hand into said user compartment, the electronic compartment including acquisition means for acquiring an image of a print of said hand part, and the user compartment further including at least one lateral opening allowing the passage of a thumb of the user's hand, wherein the lateral opening extends as far as the frontal opening to form a continuous open space, the lateral opening being delimited in a direction of insertion of the user's hand into the user compartment by a user hand positioning stop to encourage the hand to be introduced into the user compartment with the thumb spread, the positioning stop impeding full insertion of the hand, wherein the user compartment further includes a blocking hood able to block a beam of light coming from the electronic compartment at least at one of the openings that are the lateral opening and the frontal opening.

* * * * *

UNITED STATES PATENT AND TRADEMARK OFFICE
CERTIFICATE OF CORRECTION

Page 1 of 1

PATENT NO. : 11,928,883 B2
APPLICATION NO. : 17/880022
DATED : March 12, 2024
INVENTOR(S) : Joël-Yann Fourre et al.

It is certified that error appears in the above-identified patent and that said Letters Patent is hereby corrected as shown below:

On the Title Page

Item (30), the Foreign Application Priority Data should read:
--(30) Foreign Application Priority Data
Aug. 5, 2021 (FR) ....................... 21 08507--

Signed and Sealed this
Fourteenth Day of May, 2024

*Katherine Kelly Vidal*

Katherine Kelly Vidal
*Director of the United States Patent and Trademark Office*